United States Patent [19] [11] 3,983,127
Tarzia et al. [45] Sept. 28, 1976

[54] PYRROLO/3,4-b/PYRIDINES
[75] Inventors: Giorgio Tarzia, Rome; Gianbattista Panzone, Cornaredo (Milan), both of Italy
[73] Assignee: Gruppo Lepetit S.p.A., Milan, Italy
[22] Filed: Mar. 17, 1975
[21] Appl. No.: 559,092

[30] Foreign Application Priority Data
Mar. 20, 1974  United Kingdom............... 12386/74

[52] U.S. Cl. ........................ 260/295.5 B; 424/236; 424/266; 260/294.8 R; 260/296 H; 260/326.2; 260/326.47; 260/326.5 J
[51] Int. Cl.² ...................................... C07D 471/04
[58] Field of Search ................. 260/295.5 B, 296 H, 260/294.8 R

[56] References Cited
FOREIGN PATENTS OR APPLICATIONS
38-7346   5/1963   Japan............................ 260/296 HP Primary Examiner—Natalie Trousof
Assistant Examiner—R. W. Ramsuer
Attorney, Agent, or Firm—Theodore Post; C. Kenneth Bjork

[57] ABSTRACT
Pyrrolo[3,4-b]pyridines which are active as antiinflammatories and prostaglandin synthetase inhibitors and have the following general formula:

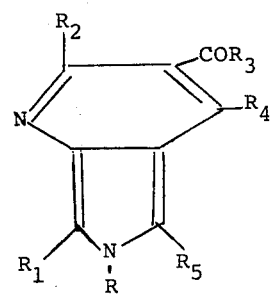

wherein:
R is $(C_{1-4})$alkyl, benzyl or chloro-substituted benzyl;
$R_1$ is hydrogen, $(C_{1-4})$alkyl, phenyl or methyl-substituted phenyl;
$R_2$ and $R_4$ independently are $(C_{1-4})$alkyl, phenyl or hydroxy;
$R_3$ is $(C_{1-4})$alkyl, $(C_{1-4})$alkoxy, or phenyl;
$R_5$ is $(C_{1-4})$alkyl; and a salt thereof with a pharmaceutically acceptable acid.

2 Claims, No Drawings

PYRROLO[3,4-b]PYRIDINES

The present invention refers to new herterocyclic compounds with pharmacological activity of the following general formula:

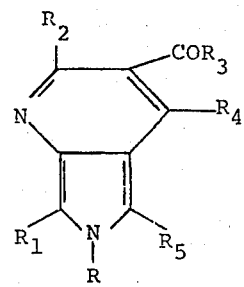

I wherein the substituents R through $R_5$ are defined as follows:

R represents hydrogen, $(C_{1-4})$alkyl, e.g. methyl, ethyl, propyl, isopropyl, butyl, isobutyl or tert-butyl, benzyl or chloro-substituted benzyl;

$R_1$ is selected from hydrogen, $(C_{1-4})$alkyl as above defined, phenyl and methyl-substituted phenyl;

$R_2$ and $R_4$ independently represent $(C_{1-4})$alkyl as above defined, phenyl or hydroxy;

$R_3$ stands for $(C_{1-4})$alkyl as above defined or $(C_{1-4})$alkoxy, e.g. methoxy, ethoxy, propoxy, isopropoxy, butoxy, isobutoxy or tert-butoxy, or phenyl;

$R_5$ represents a $(C_{1-4})$alkyl group as above defined; and to salts therewith of pharmaceutically acceptable acids.

In naming the substances of the formula I above, the rules of the I.U.P.A.C. have been followed. For the sake of better understanding the basic structure can be named pyrrolo[3,4-b]pyridine and the various positions of the heterocyclic molecule are numbered as indicated below:

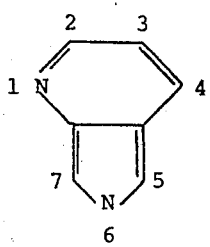

It is understandable to any person who is skilled in the art that, when one or both of $R_2$ and $R_4$ represent hydroxy, the above compounds of formula I may also exist in the corresponding tautomeric keto forms, which, accordingly, are considered as a part of the invention. This characteristic is known from the chemical literature concerning the 2-hydroxy-, 4-hydroxy- or 2,4-dihydroxypyridines as, for instance from R. C. Elderfield, Heterocyclic Compounds, Vol. 1, 525–538, John Wiley & Sons, New York, 1950.

The process for preparing the compounds of the invention substantially follows the scheme discovered by P. Friedländer, Berichte, 15, 2572, 1882, for the synthesis of quinolines. This scheme was subsequently improved and modified by other authors, as for instance, Kempter et al., Chemische Berichte, 97, 16, 1964, who applied Friedlander's synthesis for obtaining policyclic condensed compounds from o-acyl-anilines and cyclic ketones. Said process schematically comprises reacting a β-aminopyrrole of the formula

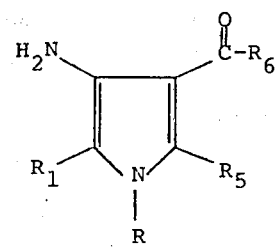

II or an acid salt thereof, in which R, $R_1$ and $R_5$ are defined as above and $R_6$ represents $(C_{1-4})$alkyl as above defined, phenyl or an alkoxy group containing from 1 to 4 carbon atoms, with a compound of formula

III in which $R_3$ has the meaning given above and X may be $(C_{1-4})$alkyl as above defined or phenyl, or, when $R_3$ represents a $(C_{1-4})$ alkoxy group, also a halogen atom.

The compounds of formula III are thus β-dicarbonyl compounds or substances which display similar properties. However, other substances acting during the reaction course as β-dicarbonyl analogs e.g. diketene or suitable β-halo-vinyl-carbonyl derivatives may be advantageously employed, and their use as the reaction partners falls within the scopes of the invention.

The reaction proceeds via the formation of an intermediate compound of formula

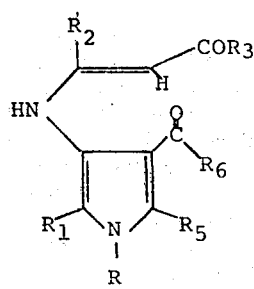

IV wherein the substituents R, $R_1$, $R_2$, $R_3$, $R_5$ and $R_6$ have the aforesaid meanings. This compound, which may exist also in the corresponding tautomeric keto form when $R_2$ represents hydroxy, can be isolated and characterized, if desired, but can also be employed as a raw product in the subsequent cyclization step. This step is performed by reacting the above intermediate compound of formula IV with a predetermined amount of a basic condensing agent.

The starting compounds of formula III or the above mentioned β-dicarbonyl analogs are commercially available products. The starting substances of formula II are prepared through a process which involves the reaction between an α-aminonitrile of formula

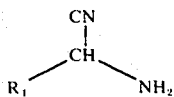

and a β-dicarbonyl compound of formula

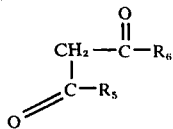

wherein $R_1$, $R_4$ and $R_5$ have the aforesaid meanings. The formed β-aminopyrrole of formula

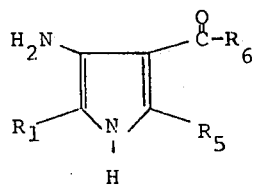

corresponding to the compound of formula II wherein R represents hydrogen can then be transformed by common chemical procedures into the other desired starting material of formula II.

According to a preferred embodiment of carrying out the invention, a compound of general formula II or an acid salt thereof is contacted with about one molar proportion of a predetermined β-dicarbonyl or β-dicarbonyl-like compound, such as, for instance, a substance of general formula III, diketene or a suitable β-halo-vinyl-carbonyl derivative, though sometimes the carbonyl reactant is conveniently employed in a slight molar excess.

The reaction proceeds quite smoothly at a temperature varying from about 0°C to the boiling temperature of the reaction mixture, and is preferably carried out in inert organic liquids, such as, for instance, benzene, toluene, dioxane, halogenated hydrocarbons containing from 1 to 4 carbon atoms, and analogs. A catalytic amount of an acid is sometimes required to speed up the reaction between the reactants of formulas II and III: suitable acids for this purpose are, for instance, acetic or p-toluenesulfonic acid.

An open chain intermediate compound of formula IV forms

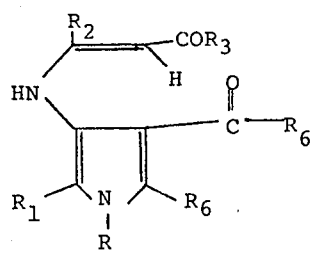

where the substituents $R, R_1, R_2, R_3, R_5$ and $R_6$ are as above defined. This compound, which exists also in the corresponding tautomeric keto form when $R_2$ is a hydroxy group, can be isolated and characterized, but can also be used as a raw product for the subsequent cyclization step without impairing the final yields. Accordingly, it is contacted in an organic solvent as, for instance, an alkanol containing from 1 to 4 carbon atoms, with a basic condensing agent which is advantageously selected from hydroxides, alkoxides or carbonates of alkali metals: among these potassium carbonate, sodium ethoxide and potassium tert-butoxide have given the best results and are employed in at least one molar proportion over the starting aminopyrrole of formula II.

The temperature at which the cyclization occurs is absolutely not critical, as it may range within very wide limits: it has been found, however, that the most favorable results are obtained if the reaction temperature is comprised between about room temperature and the reflux temperature of the reaction mixture. Generally, time intervals from about 1 to about 4 hours are sufficient to obtain the desired end products of formula I in good yields.

The compounds of formula I are recovered from the reaction medium as free bases or as the corresponding salts of pharmaceutically acceptable acids, following techniques which are entirely familiar to a skilled chemist.

For instance, they can suitably be recovered by filtration being high-melting solids, and, if necessary, purified by column chromatography or recrystallization from organic solvents.

The foregoing mentioned salts of pharmaceutically acceptable acids are essentially represented by the hydrochloride, hydrobromide, hydroiodide, sulfate, phosphate, benzoate, oxalate, acetate, methanesulfonate, cyclohexylsulfonate and analogs.

These salts possess the same degree of activity of the free bases, and accordingly, they are included within the scopes of the present invention. They are easily obtained by treating a compound of formula I as the free base with the predetermined pharmaceutically acceptable acid. In turn, it is possible to restore the free base from the corresponding salt by reaction with at least one equimolecular amount of a basic agent.

The compounds of the invention display very interesting pharmacological properties; more particularly they are active essentially as antiinflammatories and as prostaglandin synthetase inhibitors.

The antiinflammatory activity was investigated through the "carrageenin induced edema" test in rats, which was performed following substantially the operative scheme proposed by C. A. Winter et al. in Proc. Soc. Expl. Biol. Med., 111, 544, 1962. Representative experiments showed that dose levels ranging from about 20 to about 100 mg/kg. per os caused a decrease of the induced edema in the laboratory animals of at least 30% over the controls i.e. the animals in which an edema was provoked but which did not receive the substance to be investigated. It must be noted that a percent decrease of the edema of 30 is absolutely significative from the pharmacological standpoint.

These very favorable antiinflammatory properties are coupled with a low toxicity, being the $LD_{50}$ of the compounds of the invention always higher than 500 mg/kg. p.o. in mice. Toxicities were determined substantially according to the method described by Lichtfield and Wilcoxon in Journ. Pharm. Expt. Ther., 96, 99, 1949.

Furthermore, some of the compounds of the invention display interesting C.N.S. depressant properties and possess a valuable degree of activity on the hydric balance of warm blooded animals.

The compounds of the invention may be administered by various routes.

While the preferred routes of administration are oral and rectal, parenteral administration can also be employed. For oral administration, the compounds are compounded into pharmaceutical dosage forms, such as, for instance, tablets, capsules, elixirs, solutions and the like. The dosage unit may contain the usual excipients, e.g. starch, gums, fatty acids, alcohols, sugars, etc. For rectal administration the compounds are administered in the form of suppositories, admixed with conventional vehicles, such as, for example, cocoa butter, wax, spermaceti or polyoxyethyleneglycols and their derivatives. The dosage range is from about 0.05 to about 2.00 g. per day, preferably administered in divided dose.

Accordingly the present invention provides a therapeutic composition comprising as the active ingredient a compound of the invention together with a pharmaceutically acceptable carrier.

The following additional description and examples further describe the invention and the manner and process of making and using it to enable the art skilled to make and use the same and set forth the best mode contemplated by the inventors of carrying out the invention.

EXAMPLE 1

3-Acetyl-7-phenyl-2,4,5-trimethyl-6H-pyrrolo[3,4-b]pyridine.

A. To a solution of 6 g. (0.0280 mole) of 4-acetyl-3-amino-5-methyl-2-phenyl-pyrrole in 250 ml. of benzene 2.5 g. (0.0250 mole) of acetylacetone and 0.3 g. (0.0017 mole) of p-toluenesulfonic acid are added. The resulting mixture is refluxed overnight and the water which forms during this period is azeotropically distilled off. After evaporating the solvent under reduced pressure, 6.8 g. of an intermediate compound of the formula IV, which is 4-acetyl-5-methyl-3-[(1-methyl-3-oxo-1-butenyl)amino]-2-phenyl-pyrrole, are obtained.

B. 1.4 Grams (0.00474 mole) of the compound prepared under A) are dissolved in 50 ml. of methanol and the resulting solution is refluxed for four hours in the presence of 1.5 g. of potassium carbonate. After cooling the reaction mixture is poured into 150 ml. of a saturated water solution of sodium chloride. 1 Gram of a solid precipitate is obtained, corresponding to the title compound which after recrystallization from a mixture of isopropanol/water melts at 202°–204°C.

EXAMPLES 2–8

The following compounds are prepared pursuant to the two steps procedure described in Example 1, starting from the appropriate compounds of formulas II and III and using alkali metal alkoxides or carbonates as the cyclizing basic catalysts. The corresponding open chain intermediate compounds of formula IV are not isolated and characterized.

2. 3-Carbethoxy-7-phenyl-2,4,5-trimethyl-6H-pyrrolo[3,4-b] pyridine from 4-acetyl-3-amino-5-methyl-2-phenyl-pyrrole and ethyl acetoacetate. Yield 73%. M.p. 150°–151°C. The compound crystallizes in a pure form from the reaction mixture upon cooling.

3. 3-Acetyl-6-ethyl-2,5-dimethyl-4,7-diphenyl-6H-pyrrolo [3,4-b]pyridine, from 3-amino-4benzoyl-1-ethyl-5-methyl-2-phenyl-pyrrole and acetylacetone. Yield 67%. M.p. 170°–172°C (from isopropanol/water).

4. 3-Acetyl-6-butyl-2,4,5-trimethyl-7-(p-tolyl)-6H-pyrrolo [3,4-b]pyridine, from 4-acetyl-3-amino-1-butyl-5-methyl-2-(p-tolyl)-pyrrole and acetylacetone. Yield 70%. M.p. 129°–30°C (from methanol).

5. 3-Acetyl-6-butyl-2,5-dimethyl-1-phenyl-6H-pyrrolo [3,4-b]pyridine-4(1H)-one, from 3-amino-1-butyl-4-carbethoxy-5-methyl-2-phenyl-pyrrole and acetylacetone. Yield 66%. M.p. 210°–211°C (from ethanol/water).

6. 3-Acetyl-6-benzyl-2,4,5-trimethyl-7-(o-tolyl)-6H-pyrrolo [3,4-b]pyridine, from 4-acetyl-3-amino-1-benzyl-5-methyl-2-(o-tolyl)-pyrrole and acetylacetone. Yield 80%. M.p. 171°–173°C (from ethanol/diethyl ether).

7. 3-Carbethoxy-2,5-dimethyl-4,7-diphenyl-6H-pyrrolo[3,4-b]pyridine hydrochloride, from 3-amino-4-benzoyl-5-methyl-2-phenyl-pyrrole and ethyl acetoacetate. Yield 54%. M.p. 241°–43°C (from methanol/water).

8. 3-Benzoyl-2,5-diethyl-4,7-diphenyl-6H-pyrrolo[3,4-b]pyridine hydrochloride, from 3-amino-4-benzoyl-5-methyl-2-phenyl-pyrrole and benzoylacetone. Yield 62%. M.p. 253°–256°C (from methanol/water).

EXAMPLE 9

3-Acetyl-4,5-dimethyl-7-phenyl-6H-pyrrolo[3,4-b]pyridine-2(1H)-one.

A. 5.0 Grams (0.0233 mole) of 4-acetyl-3-amino-5-methyl-2-phenyl-pyrrole are suspended in 200 ml. of benzene, then 2.5 g. (0.0297 mole) of diketene are added dropwise under vigorous stirring. The mixture is refluxed for 40 minutes, then it is cooled and the solid which precipitates is recovered by filtration. M.p. 155°–58°C (from acetone/hexane). This compound is an intermediate compound of the formula IV and is 4-acetyl-3(2-acetyl)acetamido-5-methyl-2-phenyl-pyrrole.

B. A solution of 2.0 g. (0.0067 mole) of the compound prepared under (A) in 25 ml. of anhydrous ethanol is added dropwise to a solution of 0.3 g. of sodium in 10 ml. of anhydrous ethanol at room temperature. The mixture is stirred for two hours, then 50 ml. of water are added and the precipitate which forms is recovered by filtration. After recrystallization from ethanol/water 1.0 g. of the title compound are obtained. M.p. 250°–51°C.

EXAMPLES 10–12

The following compounds are prepared pursuant the two step procedures described in the foregoing Example using the appropriate aminopyrrole of formula II and diketene as the starting materials and alkali metal alkoxides or carbonates as the cyclizing basic agents. The corresponding open chain intermediate compounds of formula IV are not isolated and characterized.

10. 3-Acetyl-6-butyl-4,5-dimethyl-7-(p-tolyl)-6H-pyrrolo [3,4-b]pyridine-2(1H)-one, from 4-acetyl-3-amino-1-butyl-5-methyl-2-(p-tolyl)-pyrrole and diketene. Yield 77%. M.p. 243°–44°C (from ethanol/diethyl ether).

11. 3-Acetyl-6-benzyl-4,5-dimethyl-7-(o-tolyl)-6H-pyrrolo [3,4-b]pyridine-2(1H)-one, from 4-acetyl-3-amino-1-benzyl-5-methyl-2-(o-tolyl)-pyrrole and diketene. Yield 71%. M.p. 248°–250°C (from acetone).

12. 3-Acetyl-4,5-dimethyl-6H-pyrrolo[3,4-b]pyridine-2(1H)-one from 4-acetyl-3-amino-5-methyl-pyrrole and diketene. Yield 69%. M.p. 203°–4°C (from ethyl/acetate).

EXAMPLE 13

3-Carbethoxy-4,5-dimethyl-7-phenyl-6H-pyrrolo[3,4-b]pyridine-2(1H)-one

A. 10 Grams (0.0466 mole) of 4-acetyl-3-amino-5-methyl-2-phenyl-pyrrole are suspended in 200 ml. of chloroform which were previously added with 75 ml. of a saturated solution of sodium bicarbonate. The resulting suspension is cooled to 0°–5°C under vigorous stirring, then 8.5 g. (0.0567 mole) of malonic acid ethyl ester chloride are added dropwise, always under stirring, which is prolonged for 1 hour. The reaction mixture is extracted with chloroform and the obtained solution is brought to dryness by evaporating off the chloroform under reduced pressure. The obtained residue is recrystallized from acetone. Yield 8.0 g. of an intermediate compound of the formula IV which is 4acetyl-3-(2-carbethoxy)acetamido-5-methyl-2-phenyl-pyrrole.

B. 1.0 Grams (0.00314 mole) of the compound prepared under (A) is cyclized to give the title compound as described under point (B) of example (3), using potassium tert-butoxide instead of sodium ethoxide as the basic catalyst. Yield 0.400 g. M.p. 287°–289°C (from ethanol/water).

Typical compounds which can be prepared according to the procedures described in the foregoing Examples are:

3-Acetyl-6-ethyl-7-methyl-4-phenyl-6H-pyrrolo[3,4-b]pyridine-2-(1H)-one.
3-Carbethoxy-6-(p-chlorobenzyl)-2,7-diethyl-5-methyl-4-propyl-6H-pyrrolo[3,4-b]pyridine.
3-Benzoyl-5-butyl-6-ethyl-4-methyl-7-(2,4-dimethylphenyl)-2-phenyl-6H-pyrrolo[3,4-b]pyridine.
3-Acetyl-2,4,5,6,7-pentamethyl-6H-pyrrolo[3,4-b]pyridine.
3-Acetyl-7-butyl-2,5-dimethyl-6-propyl-6H-pyrrolo[3,4-b]pyridine-4(1H)one.
3-Acetyl-6-(o-chlorobenzyl)-2,5-dimethyl-7-phenyl-6H-pyrrolo [3,4-b]pyridine-4(1H)-one.
3-Acetyl-6-(p-chlorobenzyl)-2,4,5-trimethyl-7-phenyl-6H-pyrrolo[3,4-b]pyridine.
3-Carbethoxy-4,5-dimethyl-6H-pyrrolo[3,4-b]pyridine-2(1H)-one.
3-Carbethoxy-6-(p-chlorobenzyl)-4,5-dimethyl-7-phenyl-6H-pyrrolo[3,4-b]pyridine-2(1H)-one.
3-Carbethoxy-4,5,6-trimethyl-6H-pyrrolo[3,4-b]pyridine 2(1H)-one.
3-Acetyl-2,4,5-trimethyl-7-(2,4,6-trimethylphenyl)-6H-pyrrolo[3,4-b]pyridine.
3-Carbethoxy-2,5-diethyl-4,7-diphenyl-6H-pyrrolo[3,4-b]pyridine.
3-Acetyl-6-isopropyl-4,5-dimethyl-7-phenyl-6H-pyrrolo[3,4-b]pyridine-2(1H)-one.
3-Carbobutoxy-2,5-dimethyl-4,7-diphenyl-6H-pyrrolo[3,4-b]pyridine.

PREPARATION OF THE STARTING β-AMINOPYRROLES OF FORMULA II

A. 4-Acetyl-3-amino-5-methyl-2-phenyl-pyrrole a. A solution of 2 g. (0.015 mole) of 2-amino-2-phenylacetonitrile and 1.4 (0.014 mole) of acetylacetone in 30 ml. of anhydrous benzene is refluxed for 2 hours on an oil bath in the presence of 100 mg. of p-toluenesulfonic acid. After cooling, the reaction mixture is filtered, then the solvent is evaporated off to give an oily residue which is distilled under reduced pressure; the fraction boiling at 150°C/0.1 mmHg. is collected.

b. 0.40 Grams of sodium are dissolved in 15 ml. of anhydrous ethanol, then a solution of 2.5 g. of the fraction boiling at 150°C/0.1 mmHg. prepared as in point (a) in anhydrous ethanol is added dropwise and the mixture is allowed to stand at room temperature for 4 hours. After bubbling hydrogen chloride in the ethanol solution, a precipitate forms, which is recovered by filtration and recrystallized from ethanol/diethyl ether.

Yield 2.0 g. of the title compound as the corresponding hydrochloride which melts at 242°C (with decomposition). The title compound is obtained by extraction with ethyl acetate of an aqueous solution of the hydrochloride alkalinized with 5% sodium hydroxide. M.p. 220°C (from methanol).

According to the procedure described in the foregoing Example the following aminopyrroles of formula II have been prepared:

| COMPOUND | M.p.°C |
| --- | --- |
| B)3-Amino-4-benzoyl-5-methyl-2-phenyl-pyrrole | 203–5 |
| C)4-Acetyl-3-amino-5-methyl-pyrrole hydrochloride | 211–212 |

PREPARATION OF

D.

3-Amino-4-benzoyl-1-ethyl-5-methyl-2-phenyl-pyrrole

The synthesis of this compound starts from compound (B) which is reacted with benzaldehyde to the corresponding Schiff's base. This product is subsequently treated with sodium hydride and then with ethyliodide, whereby 3-benzylideneamino-4-benzoyl-1-ethyl-5-methyl-2-phenyl-pyrrole (M.p. 147°–148°C) is obtained. This compound is then hydrolyzed under mild acidic conditions to the title substance (M.p. 238°–240°C).

The following compounds have been prepared pursuant to the same procedure of the previous example. The melting points of the starting β-aminopyrroles, if necessary, are reported: they have been prepared substantially as described for the synthesis of compound (A).

E.
4-Acetyl-3-amino-1-butyl-5-methyl-2-(p-tolyl)-pyrrole, from
4-acetyl-3-amino-5-methyl-2-(p-tolyl)-pyrrole (M.p. 232°–234°C) M.p. of the title compound 93°–94°C.

F.
3-Amino-1-butyl-4-carbethoxy-5-methyl-2-phenyl-pyrrole hydrochloride, from
3-amino-4-carbethoxy-5-methyl-2-phenyl-pyrrole hydrochloride (m.p. 249°–252°C). M.p of the title compound 189°–192°C.

G.
4-Acetyl-3-amino-1-benzyl-5-methyl-2-(o-tolyl)-pyrrole, from
4-acetyl-3-amino-5-methyl-2-(o-tolyl)-pyrrole (m.p. 258°C) The title compound melts at 113°–15°C.

We claim:
1. A compound of the formula

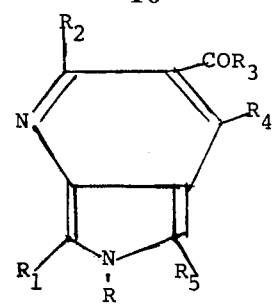

wherein
R represents hydrogen, $(C_{1-4})$alkyl, benzyl or chloro-substituted benzyl;
$R_1$ represents hydrogen, $(C_{1-4})$alkyl, phenyl or methyl-substituted phenyl;
$R_2$ and $R_4$ independently represent $(C_{1-4})$alkyl, phenyl or hydroxy;
$R_3$ represents $(C_{1-4})$alkyl or $(C_{1-4})$alkoxy;
$R_5$ represents $(C_{1-4})$alkyl; and a salt thereof with a pharmaceutically-acceptable acid.
2. The compound of claim 1 which is 3-carbethoxy-7-phenyl-2,4,5-trimethyl-6H-pyrrole[3,4-b]pyridine.

* * * * *

UNITED STATES PATENT AND TRADEMARK OFFICE
CERTIFICATE OF CORRECTION

PATENT NO. : 3,983,127
DATED : September 28, 1976
INVENTOR(S) : Giorgio Tarzia and Gianbattista Panzone It is certified that error appears in the above-identified patent and that said Letters Patent are hereby corrected as shown below:

Column 1, line 3, last word, "herterocyclic" should read -- heterocyclic --.

Column 6, line 25, "3-Benzoyl-2,5-diethyl-4,7-" etc. should read -- 3-Benzoyl-2,5-dimethyl-4,7- -- etc.

Column 7, line 28, "4acetyl-3-(2-carbethoxy)" etc. should read -- 4-acetyl-3-(2-carbethoxy) -- etc.

Column 9, line 22, "258°C) The" should read -- 258°C). The --.

Column 10, line 24, second line of Claim 2, "phenyl-2,4,5-trimethyl-6H-pyrrole[3,4-b]pyridine should read -- phenyl-2,4,5-trimethyl-6H-pyrrolo[3,4-b]pyridine --.

Signed and Sealed this

Twenty-fourth Day of May 1977

[SEAL]

Attest:

RUTH C. MASON
Attesting Officer

C. MARSHALL DANN
Commissioner of Patents and Trademarks